(12) United States Patent
Kim

(10) Patent No.: US 10,739,244 B2
(45) Date of Patent: Aug. 11, 2020

(54) SYSTEM AND METHOD FOR MONITORING CONTAMINANTS IN FLUID PASSING THROUGH PIPE IN GAS TURBINE

(71) Applicant: DOOSAN HEAVY INDUSTRIES & CONSTRUCTION CO., LTD., Changwon-si, Gyeongsangnam-do (KR)

(72) Inventor: Sang Jo Kim, Gimhae-si (KR)

(73) Assignee: Doosan Heavy Industries Construction Co., Ltd, Gyeongsangnam-do (KR)

( * ) Notice: Subject to any disclaimer, the term of this patent is extended or adjusted under 35 U.S.C. 154(b) by 0 days.

(21) Appl. No.: 16/252,787

(22) Filed: Jan. 21, 2019

(65) Prior Publication Data
US 2019/0301996 A1 Oct. 3, 2019

(30) Foreign Application Priority Data
Mar. 29, 2018 (KR) .................. 10-2018-0036251

(51) Int. Cl.
G01N 15/14 (2006.01)
G06T 7/62 (2017.01)
G06T 7/00 (2017.01)

(52) U.S. Cl.
CPC ..... *G01N 15/1429* (2013.01); *G01N 15/1434* (2013.01); *G06T 7/0008* (2013.01);
(Continued)

(58) Field of Classification Search
CPC ................................................. G01N 15/1429
(Continued)

(56) References Cited

U.S. PATENT DOCUMENTS

| | | | |
|---|---|---|---|
| 5,302,837 A * | 4/1994 | Sawa | G08B 17/113 |
| | | | 250/574 |
| 6,067,157 A * | 5/2000 | Altendorf | G01N 15/147 |
| | | | 356/337 |

(Continued)

FOREIGN PATENT DOCUMENTS

| | | |
|---|---|---|
| JP | 2000-235004 A | 8/2000 |
| JP | 2017-529526 A | 10/2017 |

(Continued)

*Primary Examiner* — Tarifur R Chowdhury
*Assistant Examiner* — Omar H Nixon
(74) *Attorney, Agent, or Firm* — Invenstone Patent, LLC

(57) ABSTRACT

A system and method monitor contaminants in fluid flowing in a structure, including contaminating particles that may be present in a fuel supplied through a pipe to a combustor of a gas turbine. The system includes a light source for projecting a light sheet on a cross-sectional area of the structure; an optical sensor for sensing particles passing through the light sheet; and a controller for controlling the light source and the sensor. A window can be formed in an outer wall of the structure, and the sensor disposed outside the structure to sense the passing particles via the window. The optical sensor acquires a monitoring image in which the particles passing through the light sheet are included, and the controller performs an image analysis on the acquired monitoring image and calculates whether contaminants are included in the fluid and a degree to which contaminants are included in the fluid.

18 Claims, 5 Drawing Sheets

(52) U.S. Cl.
CPC .......... *G06T 7/62* (2017.01); *G01N 2015/144* (2013.01); *G01N 2015/1493* (2013.01); *G01N 2015/1497* (2013.01); *G06T 2207/30232* (2013.01)

(58) Field of Classification Search
USPC ........................................................ 356/336
See application file for complete search history.

(56) References Cited

U.S. PATENT DOCUMENTS

| | | | | |
|---|---|---|---|---|
| 8,900,703 | B1* | 12/2014 | Thommana | G11C 8/20 428/402 |
| 2008/0221711 | A1* | 9/2008 | Trainer | G01N 15/0205 700/54 |
| 2012/0274760 | A1* | 11/2012 | King | G01N 15/1463 348/135 |
| 2014/0234865 | A1* | 8/2014 | Gabriel | G01N 15/1459 435/7.21 |
| 2014/0273068 | A1* | 9/2014 | Wanders | G01N 33/5094 435/29 |
| 2015/0177506 | A1* | 6/2015 | Nishiwaki | G02B 21/367 348/46 |
| 2017/0160529 | A1* | 6/2017 | Lippert | G02B 21/06 |
| 2017/0241254 | A1* | 8/2017 | Jung | G01L 3/08 |
| 2017/0269345 | A1* | 9/2017 | Siebenmorgen | G02B 5/0221 |

FOREIGN PATENT DOCUMENTS

| | | |
|---|---|---|
| JP | 2017-208384 A | 11/2017 |
| KR | 10-1999-0014696 A | 2/1999 |
| KR | 10-2002-0068045 A | 8/2002 |
| KR | 10-2003-0085749 A | 11/2003 |
| KR | 10-0912422 B1 | 8/2009 |
| KR | 10-2005-0095371 A | 9/2015 |
| KR | 10-2016-0094116 A | 8/2016 |

* cited by examiner

[FIG. 1]
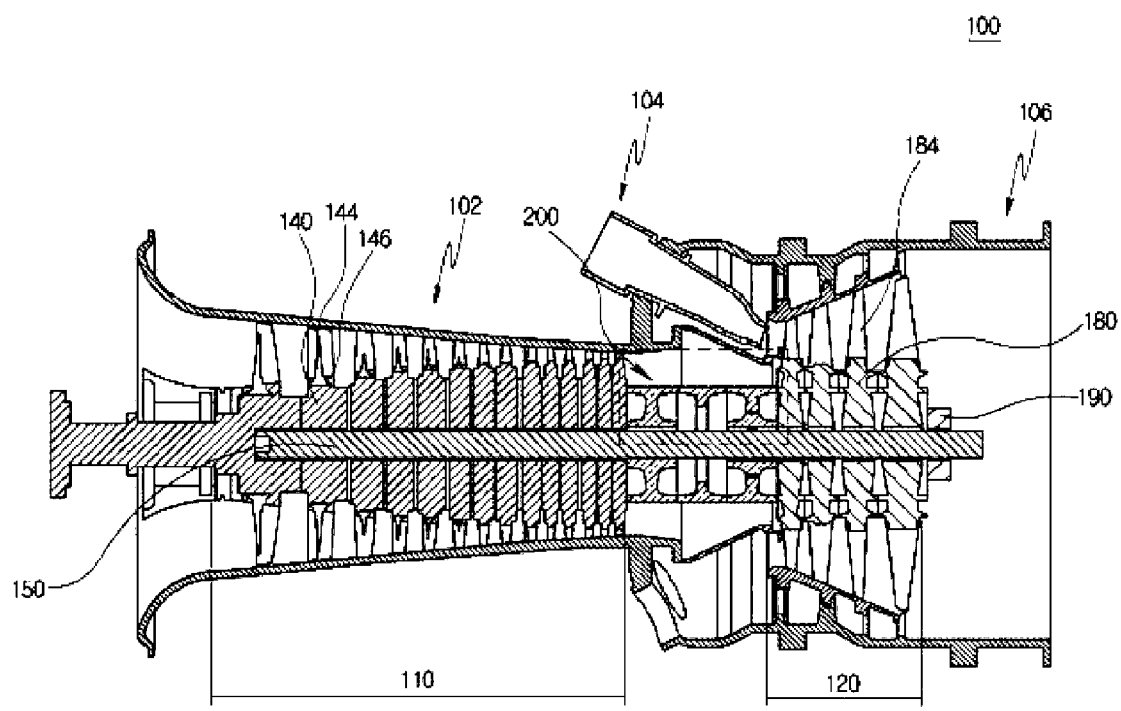

[FIG. 2]
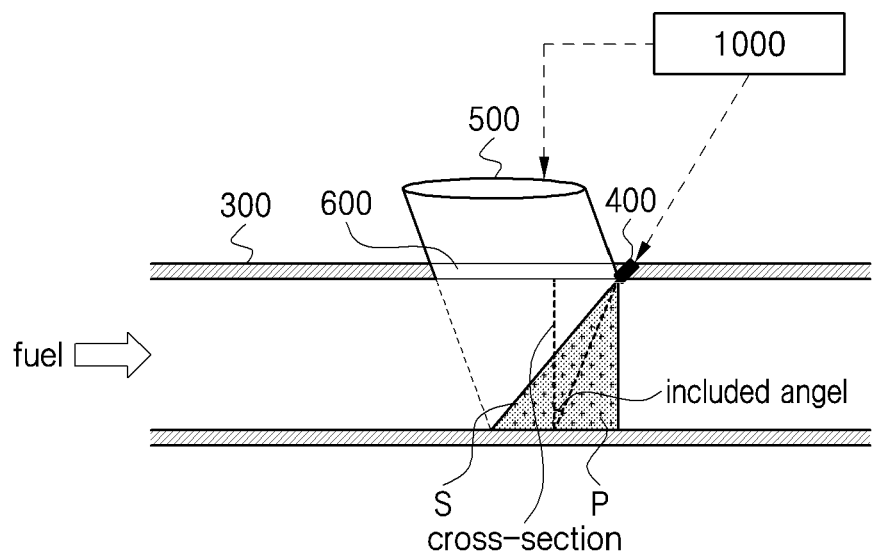

[FIG. 3]
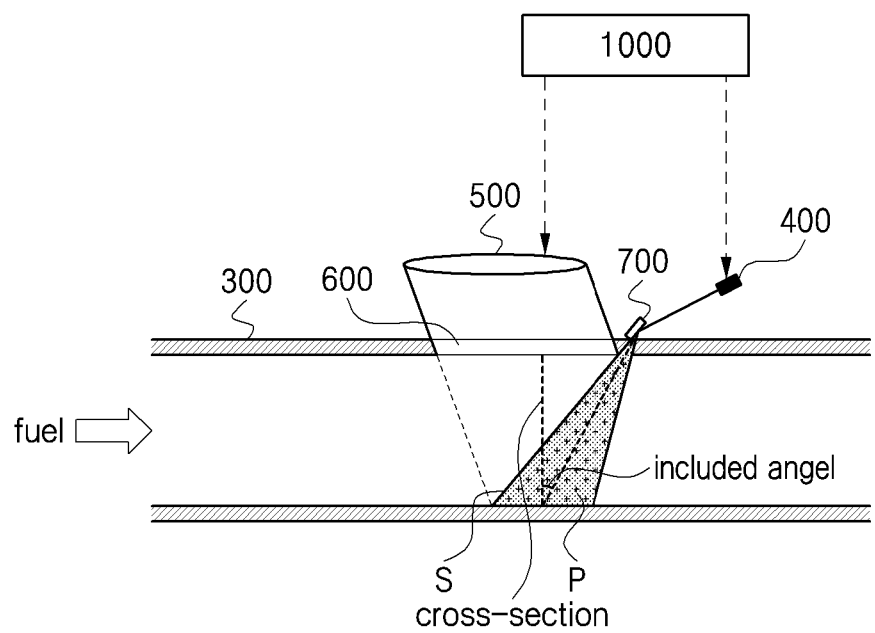

[FIG. 4]
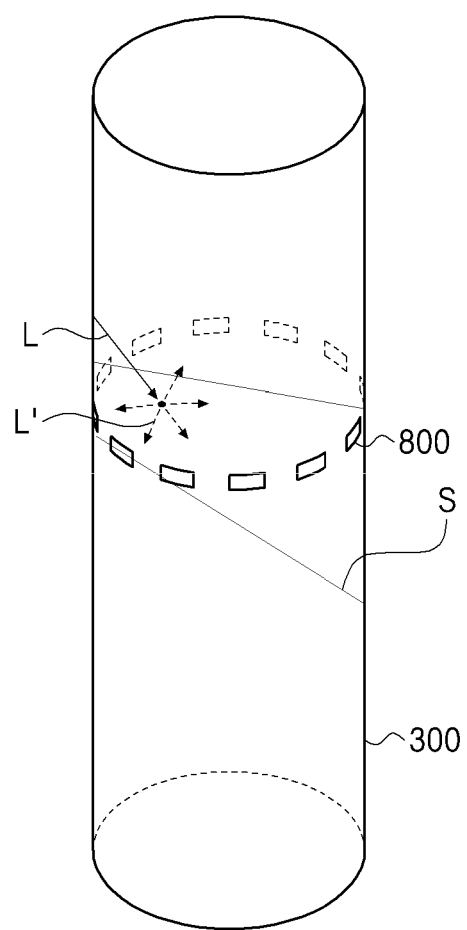

[FIG. 5]
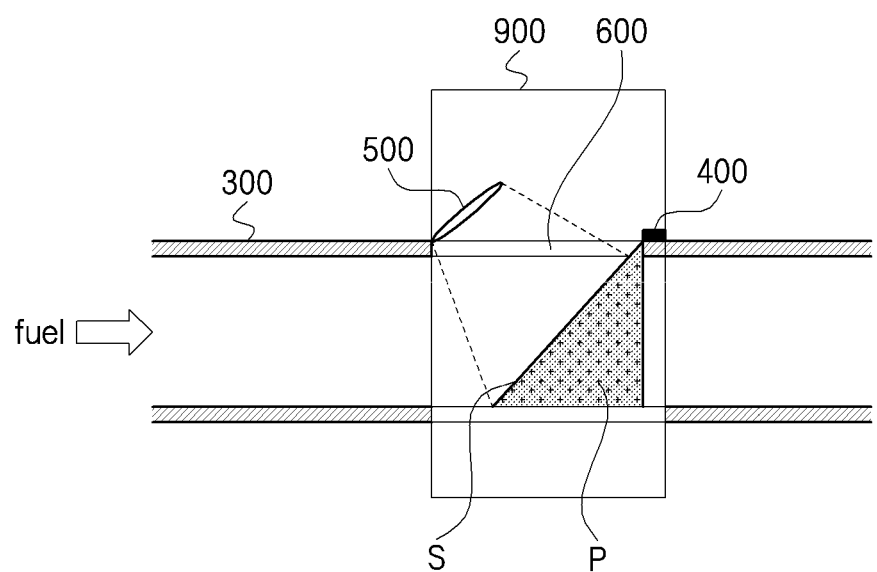

SYSTEM AND METHOD FOR MONITORING CONTAMINANTS IN FLUID PASSING THROUGH PIPE IN GAS TURBINE

CROSS-REFERENCE TO RELATED APPLICATIONS

This application claims priority to Korean Patent Application No. 10-2018-0036251, filed on Mar. 29, 2018, which is incorporated herein by reference in its entirety.

BACKGROUND OF THE DISCLOSURE

Field of the Disclosure

The present disclosure relates to a system and a method for monitoring contaminants passing through fluid, and more particularly, to a system and a method for monitoring contaminants in fluid flowing in a structure, for example, contaminating particles present in a fuel supplied through a pipe to a combustor of a gas turbine.

Description of Related Art

A turbine is a mechanical device for obtaining a rotational force by an impulsive force or a reaction force by using a flow of compressible fluid such as steam or gas. Types of turbines include a steam turbine using steam, a gas turbine using high-temperature combustion gas, etc.

Among them, the gas turbine is largely composed of a compressor, a combustor, and a turbine. The compressor is provided with an air inlet for introducing air, and a plurality of compressor vanes and compressor blades are alternately disposed in a compressor casing. The combustor supplies fuel to the compressed air compressed in the compressor and ignites it with a burner to generate high-temperature and high-pressure combustion gas. The turbine has a plurality of turbine vanes and turbine blades alternately disposed in a turbine casing. A rotor is passed through the central parts of the compressor, the combustor, the turbine, and an exhaust chamber and has opposite ends each rotatably supported by a bearing. A plurality of disks are fixed to the rotor and connected to each other. A driving shaft for a generator may be coupled to the gas turbine on the exhaust chamber side.

There are advantages in that since such a gas turbine does not have a reciprocating machine such as a piston of four-stroke engine, there may be no mutual friction parts like piston-cylinder, thus consuming very little lubricant, greatly reducing an amplitude that is the characteristic of the reciprocating machine, and performing a high-speed motion.

The gas turbine operates by the compressed air in the compressor being mixed with fuel and combusted to produce high-temperature combustion gas, which is injected into the turbine side. The injected combustion gas generates a rotational force while passing through the turbine vane and the turbine blade, thus rotating the rotor.

Meanwhile, the fuel to be mixed with the compressed air may be an essential energy supply source required for driving the gas turbine, and such fuel generally undergoes quality verification before being used. Nevertheless, fine particles and other contaminants may be present in the received fuel. In addition, corrosion or deterioration of a pipe or other components in the gas turbine may cause the flow of fuel mixed with contaminants.

The contaminants included in the fuel may result in insufficient energy being generated upon combustion, thus reducing output. In addition, an accumulation of the contaminants may cause a failure of the gas turbine. Therefore, in operating the gas turbine, it is essential to monitor the contaminants in the fuel and to take preventive or follow-up measures accordingly.

The present disclosure proposes a system and a method for monitoring contaminants in fluid flowing through a pipe in a gas turbine. The present disclosure is intended to solve the above problems, and an object of the present disclosure is to provide additional technical elements that may solve the above-described technical problems, and may not be easily invented by those skilled in the art.

SUMMARY OF THE DISCLOSURE

An object of the present disclosure is to monitor whether fine particles, that is, contaminants, are present in fluid flowing through a pipe in a gas turbine.

In particular, an object of the present disclosure is to provide a system to generate and project a light sheet on a cross-sectional inside a structure and to sense particles in fluid passing through the light sheet, thus easily and externally monitoring contaminants present in the fluid, wherein the structure may be a pipe in a combustor of a gas turbine and the fluid may be a fuel being fed to the combustor through the pipe.

Another object of the present disclosure is to provide a system in which at least one light sensing sensor is separately provided to the outer wall of the pipe in order to sense light scattered by the particles, thus monitoring the contaminants in the fluid more accurately.

Another object of the present disclosure is to provide a contaminant monitoring method for a system as above.

The technical objects of the present disclosure are not limited to the above-described technical objects, and other technical objects that are not described may be clearly understood to those skilled in the art from the following description.

In order to solve the above problem, there is provided a system for monitoring contaminants in fluid flowing in a structure. The system may include a light source for projecting a light sheet on a cross-sectional area of the structure; a sensor for sensing particles passing through the light sheet; and a controller for controlling the light source and the sensor.

The system may further include a window formed in an outer wall of the structure, and the sensor may be disposed outside the structure and is configured to sense the passing particles via the window.

The projected light sheet may form an included angle with a perpendicular cross section through a longitudinal axis of the structure.

The light source may be installed in an outer wall of the structure.

The sensor may include an optical lens and may be installed so that the normal line of the light sheet coincides with the center of the optical lens.

The sensor may include an optical sensor and is configured to acquire a monitoring image in which the particles passing through the light sheet are included.

The controller may be configured to perform an image analysis on the acquired monitoring image and to calculate according to the image analysis at least one of whether contaminants are included in the fluid and a degree to which contaminants are included in the fluid. The controller may be further configured to calculate whether the contaminants are included in the fluid by determining whether the sensed particles are contaminants based on at least one of a size and a shape of the particles included in the acquired monitoring image. The controller may be further configured to calculate the degree to which the contaminants are included in the fluid by estimating at least one of a number per unit area and a number per unit volume of the particles included in the monitoring image.

The system may further include a reflection part provided on an outer wall of the structure and configured to reflect the light from the light source, and the light source may be disposed outside the structure and may irradiate light toward the reflection part, so that the light sheet is projected on the cross-sectional area. The outer wall of the structure may include at least one aperture through which the reflected light may pass.

The system may further include at least one light sensing sensor installed in the outer wall of the structure. The at least one light sensing sensor may be configured to sense light scattered by the particles in the fluid. The controller may be configured to calculate at least one of whether contaminants are included in the fluid and a degree to which contaminants are included, based on the acquired monitoring image and the sensing of the at least one light sensing sensor.

The system may further include a case surrounding the structure, and the light source and the sensor may be disposed inside the case. The case may have a donut shape.

The controller may be configured to control operation time, operation period, and operation cycle of each of the light source and the sensor.

According to another aspect of the present disclosure, there is proved a method for monitoring contaminants in fluid flowing in a structure. The method may include projecting a light sheet on a cross-sectional area of the structure; sensing particles passing through the light sheet; and calculating, according to the sensing, at least one of whether contaminants are included in the fluid and a degree to which contaminants are included in the fluid. The method may further include acquiring a monitoring image in which the particles passing through the light sheet are included; and performing an image analysis on the acquired monitoring image. The sensing may include sensing light scattered by the particles in the fluid by at least one light sensing sensor installed in an outer wall of the structure.

According to the present disclosure, it is possible to form a light sheet in the pipe to easily observe the particles passing through the light sheet, thus easily monitoring the contaminants in the fluid.

In addition, according to the present disclosure, it is possible to change the angle of irradiating the light into the pipe to adjust an included angle formed with a perpendicular cross section of the pipe as created by the light sheet, thus adjusting the area of the light sheet in the pipe, such that a user may define the area to be monitored.

In addition, according to the present disclosure, it is possible not only to provide the optical sensor for photographing particles passing through the light sheet, thus easily monitoring the passing particles, but also to provide an additional light sensing sensor on the outer wall of the pipe, thus sensing light scattered by the particles to confirm the presence or absence of the particles more clearly.

The effects of the present disclosure are not limited to the above-mentioned effects, and other effects that are not described may be clearly understood to those skilled in the art from the following description.

BRIEF DESCRIPTION OF THE DRAWINGS

FIG. 1 is a cross-sectional view of a gas turbine to which may be applied a contaminant monitoring system according to the present disclosure.

FIG. 2 is a diagram of a cross section of a pipe for illustrating a first embodiment of a contaminant monitoring system according to the present disclosure.

FIG. 3 is a diagram of a cross section of a pipe for illustrating a second embodiment of a contaminant monitoring system according to the present disclosure.

FIG. 4 is a perspective view of a pipe for illustrating a third embodiment of a contaminant monitoring system in which a plurality of light sensing sensors are provided on the outer wall of the pipe to sense light scattered by particles.

FIG. 5 is a diagram of a cross section of a pipe for illustrating a fourth embodiment of a contaminant monitoring system in which a case surrounds the pipe.

DESCRIPTION OF SPECIFIC EMBODIMENTS

Hereinafter, preferred embodiments of the present disclosure will be described in detail with reference to the accompanying drawings. The advantages and features of the present disclosure, and a method for achieving them will become apparent with reference to the embodiments that will be described in detail later together with the accompanying drawings. However, the present disclosure is not limited the embodiments disclosed below but may be embodied in various forms; these embodiments are only provided so that the present disclosure is complete and is provided to fully convey the scope of the disclosure to those skilled in the art; and the present disclosure is only defined by the scope of the claims. The same reference numerals refer to the same components throughout the specification.

Unless otherwise defined, all terms (including technical and scientific terms) used in the present specification have the same meaning as commonly understood by those skilled in the art to which the present disclosure pertains.

In addition, terms defined in commonly used dictionaries will not be interpreted in an idealized or overly formal sense unless expressly and especially defined herein. The terminology used in the present specification is for the purpose of describing embodiments only and is not intended to limit the present disclosure. In the present specification, the singular forms are intended to include the plural forms as well, unless the context clearly indicates otherwise.

The terms "comprises" and/or "comprising," or "includes" and/or "including" when used in this specification, specify the presence of stated components, steps, operations, and/or elements, but do not preclude the presence or addition of one or more other components, steps, operations, and/or elements.

First, the structure of a gas turbine will be described with reference to FIG. 1, illustrating an example of a gas turbine 100 according to the present disclosure.

Referring to FIG. 1, the gas turbine 100 includes a housing 102 through which combustion gas is passed through the turbine and a diffuser 106, through which the combustion gas having passed through the turbine is discharged, provided at the rear side of the housing 102. A combustor 104 for receiving and combusting compressed air is disposed toward the front side of the diffuser 106.

Explaining based on the flow direction of the air, a compressor section 110 is disposed at the upstream side of the housing 102, and a turbine section 120 is disposed at the downstream side. A torque tube 200, serving as a torque transmission member for transmitting a rotational torque generated in the turbine section to the compressor section, may be interposed between the compressor section 110 and the turbine section 120.

The compressor section 110 is provided with a plurality of compressor rotor disks 140, and the respective compressor rotor disks 140 are fastened together by a tie rod 150 so as to not be spaced apart in the axial direction.

Specifically, the respective compressor rotor disks 140 are substantially arranged along the axial direction and have centers penetrated by the tie rod 150. Here, neighboring compressor rotor disks 140 are disposed such that their opposing surfaces are compressed against each other by the tie rod 150 and do not exhibit relative rotation.

A plurality of blades 144 are radially coupled to the outer circumferential surface of the compressor rotor disk 140. Each of the blades 144 has a root part 146 to be fastened to the compressor rotor disk 140.

A vane (not illustrated) fixedly disposed to the housing is interposed between the respective compressor rotor disks 140. Thus, unlike the rotor disk, the fixed vane does not rotate but aligns the flow of the compressed air having passed through the blade of an upstream compressor rotor disk to guide the air to the blade of the next (downstream) rotor disk.

A fastening type of the root part 146 includes a tangential type and an axial type. This may be selected according to the required structure of the commercial gas turbine and may have a commonly known dovetail or fir-tree configuration. Other fastening means are possible using, for example, a fixture such as a key or a bolt.

The tie rod 150, which is passed through the central parts of the plurality of compressor rotor disks 140, has one end fastened in the farthest upstream compressor rotor disk. The tie rod 150 may be variously configured according to the gas turbine, and its structure is not necessarily limited to the single tie rod illustrated in FIG. 1. For example, the tie rod may be configured such that a plurality of tie rods are disposed in the circumferential direction, or a combination of the single and plural tie rods may be used.

Although not illustrated, the compressor of the gas turbine may be provided with a guide vane, called a deswirler, which is arranged next to the diffuser in order to increase a pressure of fluid and then match a flow angle of the fluid entering the inlet of the combustor to a design flow angle.

The combustor 104 mixes the received compressed air with fuel and combusts the mixture to generate the high-temperature and high-pressure combustion gas of high energy. Through an isobaric combustion process, the combustor 104 increases a combustion gas temperature to a heat resistance limit of the combustor and other turbine components.

The combustor 104 generally consists of a plurality of combustor constituting a combustion system of the gas turbine. Each of the plural combustors is arranged in a casing formed as a cell configured to include a burner including a fuel injection nozzle, etc., a combustor liner for forming a combustion chamber, and a transition piece that becomes a connection part of the combustor and the turbine.

Specifically, the liner of a combustor cell provides a combustion space in which the fuel injected by the fuel nozzle is mixed with the compressed air of the compressor and combusted. Such a liner may include a crossfire tube for providing the combustion space in which the fuel mixed with air is combusted, and a flow sleeve for forming an annular space while surrounding the crossfire tube. In addition, the fuel nozzle is coupled to the front end of the liner, and an ignition plug is coupled to the side wall thereof.

The transition piece is connected to the rear end of the liner so that the combustion gas combusted by the ignition plug may be sent to the turbine side. The transition piece has the outer wall part cooled by the compressed air supplied from the compressor in order to prevent damage due to a high temperature of the combustion gas. For this purpose, the transition piece is provided with holes for cooling in order to inject air to its interior and thus cool the transition piece body, after which the compressed air flows to the liner side. The cooling air having cooled the transition piece flows in the annular space of the liner, and the compressed air from the outside of the flow sleeve may be supplied to the cooling air through the cooling holes prepared in the flow sleeve part to collide with the outer wall of the liner.

Meanwhile, the high-temperature and high-pressure combustion gas coming from the combustor is supplied to the turbine section 120. As the supplied combustion gas provides an impulsive force and a reaction force to the rotating wing of the turbine while expanding to generate a rotational torque, the rotational torque thus obtained is transmitted to the compressor section 110 through the torque tube 200, and the power exceeding the power required for driving the compressor is used for driving a generator or similar apparatus.

The turbine section has a structure fundamentally similar to that of the compressor section. For example, the turbine section 120 is provided with a plurality of turbine rotor disks 180 similar to the compressor rotor disks of the compressor section 110 and a plurality of turbine blades 184 radially disposed on each disk. Further similarities include the turbine blade 184 being coupled to the turbine rotor disk 180 in a dovetail manner or the like, and a vane (not illustrated) fixed to the housing and provided between the blades 184 of the turbine rotor disk 180 to guide the flow direction of the combustion gas having passed through the blade.

As described above, the schematic structure of the gas turbine according to the present disclosure has been described. A contaminant monitoring system according to the present disclosure may be coupled to the combustor 104 of the above-described gas turbine structure and may be particularly provided inside the nozzle in a pipe connected to the combustor 104, that is, a structure in which fluid such as fuel flows.

Hereinafter, referring to FIGS. 2 to 5, the contaminant monitoring system according to the present disclosure will be described in detail.

Referring to FIG. 2 illustrating a first embodiment of a contaminant monitoring system, the system may include a pipe 300, a light source 400, and a sensor unit 500.

Although not specifically illustrated in FIG. 2, the contaminant monitoring system according to the present disclosure may further include a control unit for controlling the light source 400 and the sensor unit 500.

Typically, the pipe 300 is a cylinder type structure in which fluid such as fuel flows, and may be understood as a structure in which fluid flows and which includes an inner space established by an outer wall forming the outer surface of the structure. In addition, the pipe 300 may include an inlet and an outlet, the inlet being configured to be connected to a fuel supply source and the outlet being configured to be connected to a fuel consumption unit, e.g., the combustor of a gas turbine. The pipe 300 may be further provided with a valve (not shown), which is controllable and may be set between fully opened and fully closed positions to control a fuel flow from each fuel supply source to the fuel consumption unit.

The light source 400 is a configuration for generating and projecting a light sheet (S) on a cross-sectional area of the pipe 300. The light source 400 may utilize a technology consistent with light sheet microscopy, which is also referred to as single plane illumination microscopy (SPIM) whereby the optical paths of illumination and detection are decoupled.

As seen in FIG. 2, the light source 400 irradiates light in a "surface" shape (i.e., a plane) upon irradiation, such that ultimately within the pipe 300, the fluid passes through the pipe 300 and at the same time, outputs the light in a surface shape in order to pass through the light sheet S as well. Meanwhile, the cross section of the pipe 300 refers to an area formed by theoretically cutting the pipe 300 across its longitudinal axis, and at this time, it should be understood that the cross section is not necessarily perpendicular to the axis. That is, the area of the cross section may be obtained by cutting the pipe 300 obliquely. Thus, the light sheet S may be projected so as to pass through the pipe 300 in the direction in which the light source 400 irradiates light, or may be projected so as to pass through the pipe 300 and form a predetermined included angle with the perpendicular cross section of the pipe 300.

The light source 400 may be installed in the outer wall of the pipe 300 and may project the light sheet S at different angles according to a direction in which the light source 400 irradiates light. FIG. 2 shows an embodiment in which the light source 400 is inclined so that the light sheet S may be formed diagonally through the pipe 300.

The sensor unit 500 is a configuration for sensing particles P in fluid when the fluid passes through the light sheet S projected by the light source 400 as described above. The fluid may include fine particles (contaminants) due to poor fuel quality or due to corrosion of the pipe 300, and the sensor unit 500 senses whether the corresponding particles P are present in the fuel as the fuel passes through the light sheet S.

The sensor unit 500 is preferably an optical sensor and may include a charge-coupled device (CCD), which is a semiconductor element, as a sensing means to acquire a video or still image received by the CCD from a target to be sensed. The sensor unit 500 may digitally convert the video or image thus acquired. As described above, when the sensor unit 500 is implemented as an optical sensor, the optical sensor may sense whether the particles P are present by acquiring a video or image of the particles P in the fluid passing through the light sheet S. The video or image acquired by the sensor unit 500 will be herein referred to as a monitoring image.

The sensor unit 500 may be provided outside the pipe 300, and when implemented as an optical sensor, the sensor unit 500 necessitates formation of a window portion 600 in the outer wall of the pipe 300, that is, a transparent area of the outer wall, in order to acquire the monitoring image of the particles P passing through the light sheet S. The window portion 600 enables the sensing of the light sheet S through the window portion 600 by the sensor unit 500 disposed outside the pipe 300.

In addition, the sensor unit 500 may be installed at a varying angle according to the angle at which the light sheet S is formed in a space in the pipe 300. In particular, when the sensor unit 500 is implemented as an optical sensor, the installation angle should be adjusted and provided to face the light sheet S, and preferably, the optical sensor may be installed so that the normal line of the light sheet S coincides with the center of a lens of the optical sensor. It should be understood, however, that this is only one embodiment, and that the optical sensor may be provided in other manners.

Lastly, the control unit is a configuration capable of controlling the light source 400 and the sensor unit 500 as described above, and generally controls the operations of the light source 400 and the sensor unit 500, such as operation time, operation period, and operation cycle of each of the light source 400 and the sensor unit 500.

Meanwhile, the control unit may perform a function of analyzing the monitoring image received from the sensor unit 500, which may be performed in addition to the general control of the light source 400 and the sensor unit 500. Once the monitoring image is acquired by the sensor unit 500 to photograph the particles P passing through the light sheet S as described above, the control unit may perform the image analysis on the monitoring image to further calculate additional information relevant to the particles P.

For example, the control unit may calculate new information such as whether the corresponding particles P are contaminants and, if they are contaminants, may further determine what type of contaminants they are, based on the sizes and shapes of the particles P included in the monitoring image. Such a calculation procedure may be performed by referencing a storage unit (not illustrated) and comparing the new information with that previously stored in the storage unit. In addition, the control unit may also calculate additionally the degree at which contaminants are included in the fuel by estimating, based on the acquired monitoring image, the number of particles per unit area, the number of particles per unit volume, etc.

The additional information thus calculated may be provided to a user through a user interface connected with the contaminant monitoring system according to the present disclosure, and the user may utilize such information to confirm a current operation state of the gas turbine, an injection state of fuel, a state of aging of the pipe 300, etc.

Meanwhile, the above-described control unit may include a controller (not shown) in the form of a microcontroller, a microprocessor, a microcomputer, etc. In addition, the control unit may be implemented as hardware, as firmware or software, or as a combination thereof. In case of implementation as hardware, the hardware may be configured to include an application specific integrated circuit (ASIC) or a digital signal processor (DSP), a digital signal processing device (DSPD), a programmable logic device (PLD), a field programmable gate array (FPGA), etc.; and in case of implementation as firmware or software, the firmware or software may be configured to include a module, a procedure, a function, etc. for performing the above-described functions or operations.

In addition, the above-described storage unit of the control unit may be implemented as a read-only memory (ROM), a random access memory (RAM), an erasable programmable read-only memory (EPROM), an electrically erasable programmable read-only memory (EEPROM), a flash memory, a static RAM (SRAM), a hard disk drive (HDD), a solid state drive (SSD), etc.

FIG. 3 illustrates a structure of a contaminant monitoring system according to a second embodiment of the present disclosure. The contaminant monitoring system of FIG. 3 is similar to that of FIG. 2 described above, except that the light source 400 is provided outside the pipe 300, and a reflection part 700 is further provided to induce the light from the light source 400 into the pipe 300.

Since the light source 400 itself generally has a volume that is not so small, it may be difficult to provide the light source 400 in the outer wall of the pipe 300. When it is difficult to provide the light source 400 in the outer wall of the pipe 300, the light source 400 may be provided outside the pipe 300, in which case a means of reflecting light into the pipe 300 is needed in order to project the light sheet S in an inner space of the pipe 300. In the present embodiment, the reflection part 700, for example, a mirror or the like, may be provided on the outer wall of the pipe 300 to project the light sheet S inside the pipe 300 through the reflection of light. Accordingly, in the present embodiment, the light source 400 may be disposed in a space away from the pipe 300, thus overcoming installation limitations. In addition, as long as the reflection part 700 may reflect light, there is no particular restriction on its structure or size, such that the reflection part 700 may be relatively and easily provided on the outer wall of the pipe 300 having a relatively thin thickness. Therefore, when the contaminant monitoring system is implemented as in the embodiment of FIG. 3, it is possible to manufacture and produce the structure itself more easily than in FIG. 2.

Meanwhile, in order to implement the system of the embodiment as in FIG. 3, it is preferable to form an aperture through which light may pass on the outer wall of the pipe. Light reflected by the reflection part may pass through the aperture.

FIG. 4 illustrates a contaminant monitoring system according to a third embodiment of the present disclosure. In addition to the light source 400 for generating the light sheet S and the sensor unit 500 for sensing the particles P passing through the light sheet S, the embodiment of FIG. 4 further includes a light sensing sensor 800 installed on the outer wall of the pipe 300. The light sensing sensor 800 may consist of a plurality of light sensing sensors 800 installed so as to be spaced apart along the outer wall of the pipe 300.

Each light sensing sensor 800 includes a device capable of sensing scattered light L' when any light L has been scattered by the particles P in the fluid. That is, in addition to acquiring the monitoring image on the particles P passing through the light sheet S using the optical sensor (the sensor unit 500), the present embodiment further includes the light sensing sensor 800 capable of sensing the scattered light, thus further increasing the accuracy of sensing contaminants.

Meanwhile, any light irradiated toward the particles P may be the same as the light irradiated by the light source 400 to project the light sheet S as described above, or may be light irradiated independently from a second light source (not shown), that is, a light source provided separately from the light source 400. At this time, the second light source may irradiate light having a wavelength different from that of the light source 400.

As described above, the contaminant monitoring system according to the present disclosure may generate and project the light sheet S to sense the particles P passing through the light sheet S, and at the same time, may further sense the scattered light scattered by the particles P, thus confirming whether the contaminants in the fluid are present more accurately.

FIG. 5 illustrates a contaminant monitoring system according to a fourth embodiment of the present disclosure, in which the contaminant monitoring system further includes a case 900 surrounding the pipe 300 and may be implemented by providing the light source 400 and the sensor unit 500 in the case 900. The case 900 may be, for example, a donut shape surrounding the pipe 300. The donut shape of the case 900 may include a central hole having an inner diameter accommodating passage of the pipe 300. As seen in FIG. 5, the light source 400 and the sensor unit 500 may be disposed inside the case 900, and a window portion 600 of the outer wall of the pipe 300 may be arranged inside the case 900. The window portion 600 may be formed of a transparent material enabling the sensor unit 500 to monitor, via the window portion 600, the particles P passing through the light sheet S.

Meanwhile, the case 900 is preferably formed of the same material as the pipe but may be formed of dissimilar materials. Also, the shape of the case 900 is not limited to a donut shape and may have any shape suitable for accommodating the light source and the sensor unit.

Although the embodiments of the present disclosure have been described with reference to the accompanying drawings, those skilled in the art to which the present disclosure pertains will understand that the present disclosure may be embodied in various specific forms without changing the technical spirit thereof or the essential features thereof. Therefore, it should be understood that the above-described embodiments are illustrative in all respects and are not limited thereto.

What is claimed is:

1. A system for monitoring contaminants in fluid flowing in a structure, the system comprising:
a light source for projecting a light sheet on a cross-sectional area of the structure, the projected light sheet extending across an inner space of the structure from a first inner surface of the structure to a second inner surface opposite to the first inner surface;
an optical sensor disposed outside the structure and configured to sense particles passing through the light sheet by acquiring a monitoring image in which the particles passing through the light sheet are included;
at least one light-sensing sensor installed on an inner surface of the outer wall of the structure and configured to sense light scattered by the particles in the fluid; and
a controller for controlling the light source and the optical sensor,
wherein the optical sensor is installed at an angle controlled by the controller so that the normal line of the light sheet coincides with the center of an optical lens of the optical sensor.

2. The system of claim 1, further comprising:
a window formed in an outer wall of the structure,
wherein the optical sensor is configured to sense the passing particles via the window.

3. The system of claim 1, wherein the projected light sheet forms an included angle with a perpendicular cross section through a longitudinal axis of the structure.

4. The system of claim 1, wherein the light source is installed in an outer wall of the structure.

5. The system of claim 1, wherein the controller is configured to perform an image analysis on the acquired monitoring image and to calculate according to the image analysis at least one of whether contaminants are included in the fluid and a degree to which contaminants are included in the fluid.

6. The system of claim 5, wherein the controller is further configured to calculate whether the contaminants are included in the fluid by determining whether the sensed particles are contaminants based on at least one of a size and a shape of the particles included in the acquired monitoring image.

7. The system of claim 5, wherein the controller is further configured to calculate the degree to which the contaminants are included in the fluid by estimating at least one of a number per unit area and a number per unit volume of the particles included in the monitoring image.

8. The system of claim 1, further comprising:
a reflection part provided on an outer wall of the structure and configured to reflect the light from the light source,
wherein the light source is disposed outside the structure and irradiates light toward the reflection part so that the light sheet is projected on the cross-sectional area.

9. The system of claim 8, wherein the outer wall of the structure includes at least one aperture through which the reflected light may pass.

10. The system of claim 1,
wherein the controller is configured to calculate at least one of whether contaminants are included in the fluid and a degree to which contaminants are included, and
wherein the calculation is based on the monitoring image acquired by the optical sensor and the scattered light sensed by the at least one light-sensing sensor.

11. The system of claim 1, further comprising a case surrounding the structure,
wherein the structure includes a first end and a second end, the fluid flowing in the structure from the first end to the second end,
wherein the light source and the optical sensor are disposed outside the structure between the first and second ends and are disposed inside the case, and
wherein the case is configured to surround only a portion of the structure between the first and second ends and the surrounded portion excludes portions of the structure disposed between the surrounded portion and either of the first and seconds ends.

12. The system of claim 11, wherein the case has a donut shape.

13. The system of claim 1, wherein the controller is configured to control operation time, operation period, and operation cycle of each of the light source and the optical sensor.

14. The system of claim 1, wherein the at least one light-sensing sensor includes a plurality of light-sensing sensors respectively installed on the inner surface of the outer wall of the structure and spaced apart from each other in a circumferential direction of the outer wall.

15. A method for monitoring contaminants in fluid flowing in a structure, the method comprising:
projecting a light sheet on a cross-sectional area of the structure, the projected light sheet extending across an inner space of the structure from a first inner surface of the structure to a second inner surface opposite to the first inner surface;
sensing particles passing through the light sheet by
controlling an installation angle of an optical sensor for sensing the particles so that the normal line of the light sheet coincides with the center of an optical lens of the optical sensor, the optical sensor disposed outside the structure and configured to sense the particles passing through the light sheet by acquiring a monitoring image in which the particles passing through the light sheet are included, and
sensing light scattered by the particles in the fluid by at least one light sensing sensor installed on an inner surface of the outer wall of the structure; and
calculating, according to the sensing, at least one of whether contaminants are included in the fluid and a degree to which contaminants are included in the fluid.

16. The method of claim 15, further comprising:
performing an image analysis on the acquired monitoring image.

17. The method of claim 15, wherein the at least one light-sensing sensor includes a plurality of light-sensing sensors respectively installed on the inner surface of the outer wall of the structure and spaced apart from each other in a circumferential direction of the outer wall, and the sensing light scattered by the particles in the fluid comprises sensing light scattered in a plurality of directions.

18. The method of claim 15, wherein the calculation is based on the monitoring image acquired by the optical sensor and the scattered light sensed by the at least one light-sensing sensor.

* * * * *